United States Patent
Wu et al.

(10) Patent No.: US 7,365,835 B2
(45) Date of Patent: Apr. 29, 2008

(54) DARK-FIELD LASER-SCATTERING MICROSCOPE FOR ANALYZING SINGLE MACROMOLECULES

(75) Inventors: Sheng Wu, San Gabriel, CA (US); Yongchun Tang, Walnut, CA (US)

(73) Assignee: California Institute of Technology, Pasadena, CA (US)

( * ) Notice: Subject to any disclaimer, the term of this patent is extended or adjusted under 35 U.S.C. 154(b) by 326 days.

(21) Appl. No.: 11/004,492

(22) Filed: Dec. 2, 2004

(65) Prior Publication Data

US 2005/0237525 A1    Oct. 27, 2005

Related U.S. Application Data

(60) Provisional application No. 60/526,334, filed on Dec. 2, 2003.

(51) Int. Cl.
*G01N 21/00* (2006.01)
(52) U.S. Cl. .................. 356/237.3; 356/237.1
(58) Field of Classification Search ............. 356/237.3, 356/336, 338; 435/6
See application file for complete search history.

(56) References Cited

U.S. PATENT DOCUMENTS

| | | | | |
|---|---|---|---|---|
| 3,646,352 A | * | 2/1972 | Bol et al. ................ 250/205 |
| 3,850,525 A | * | 11/1974 | Kaye ........................ 356/73 |
| 4,541,719 A | * | 9/1985 | Wyatt ....................... 356/343 |
| 4,595,291 A | * | 6/1986 | Tatsuno .................... 356/336 |
| 4,661,913 A | * | 4/1987 | Wu et al. .................. 702/19 |
| 4,676,641 A | * | 6/1987 | Bott ......................... 356/336 |
| 4,679,939 A | * | 7/1987 | Curry et al. .............. 356/336 |
| 4,775,943 A | * | 10/1988 | Chamberlin et al. ...... 702/30 |
| 4,890,920 A | * | 1/1990 | Niziolek et al. .......... 356/336 |
| 5,056,918 A | * | 10/1991 | Bott et al. ................ 356/336 |
| 5,104,221 A | * | 4/1992 | Bott et al. ................ 356/336 |
| 5,185,641 A | * | 2/1993 | Igushi et al. ............. 356/336 |
| 5,540,494 A | * | 7/1996 | Purvis et al. ............. 356/73 |

(Continued)

OTHER PUBLICATIONS

Giovanni Cappello, Mathilde Badoual, Albrecht Ott, Jacpues Prost and Lorenzo Busoni, Physical Review 2003, E 68, 021907.

(Continued)

*Primary Examiner*—Layla G. Lauchman
*Assistant Examiner*—Jarreas Underwood
(74) *Attorney, Agent, or Firm*—Tope-McKay & Associates

(57) ABSTRACT

To further isolate the scattered light 112 of a specific particle from the scattered light of a different particle, a pin hole device 116 can be used. The pin hole device 116 prevents unfocused light from other particles from entering the second plane 118, thus isolating a desired, focused image of one particle 110 of the sample 106. In one embodiment, the pin hole 116 has a size of several microns. At the second plane 118, a traditional imaging detection device 120 detects the defocused light. The position of the second image plane 118 is chosen for good angular resolution of the scattered light 112, and at the same time gives enough light for the imaging detection device 120 to obtain a sufficient reading.

13 Claims, 1 Drawing Sheet

U.S. PATENT DOCUMENTS

| | | | |
|---|---|---|---|
| 5,576,827 A * | 11/1996 | Strickland et al. | 356/336 |
| 5,995,866 A * | 11/1999 | Lemelson | 600/476 |
| 6,533,912 B2 * | 3/2003 | Mansfield et al. | 204/457 |
| 6,646,742 B1 * | 11/2003 | Gangstead et al. | 356/342 |
| 6,999,166 B2 * | 2/2006 | Matsushita et al. | 356/317 |
| 7,170,597 B1 * | 1/2007 | Hooper et al. | 356/317 |
| 2002/0173045 A1 * | 11/2002 | Schwartz | 436/164 |

OTHER PUBLICATIONS

Warren Wiscombe, "Improved Mie Scattering Algorithms," Appl. Opt. 19(9), 1505-1509, 1980.

Nada N. Boustany, Rebekah Drezek, and Nitish V. Thakor, Biophysical Journal vol. 83, Sep. 2002, 1691-1700.

* cited by examiner

DARK-FIELD LASER-SCATTERING MICROSCOPE FOR ANALYZING SINGLE MACROMOLECULES

PRIORITY CLAIM

The present application claims the benefit of priority of U.S. Provisional Patent Application No. 60/526,334, filed Dec. 2, 2003, entitled "Laser Scattering Microscope that Constructs Three-Dimensional Picture."

STATEMENT OF GOVERNMENT INTEREST

This invention described herein was made in the performance of work under a DOE contract, and is subject to the provisions of Public Law 96-517 (35 USC 202) in which the Contractor has elected to retain title.

BACKGROUND OF THE INVENTION (1) Technical Field

The present invention relates to a dark-field laser-scattering microscope for analyzing single macromolecules. More specifically, the present invention relates to a microscope with a variable wavelength, movable laser with well-defined direction for dark-field light-scattering of macromolecules in-vivo to reveal characteristics such as size, shape, molecular weight, and refractive index. The microscope is capable of constructing a three-dimensional image of a sample, with the use of a computer, without separating the sample from the in-vivo environment or contaminating the sample with fluorescent dyes.

(2) Background

There is great interest in analyzing single macromolecules with sizes well below 1 micron without having to separate them from the in-vivo environment. For example, certain vesicles, viruses, micro crystals, polymers and wax formations would be ideal candidates for analysis in their native environments.

Traditional microscopes must collect the transmitting part of the illumination light beam and then construct a two-dimensional image based upon the loss of photons. Traditional microscopes cannot image tiny particles with lateral sizes under one half of the illumination wavelength because of the diffraction limit. However, laser scattering could illuminate particles well below this limit, down to 10 nanometers, and still be detected by traditional charge-coupled devices (CCDs).

Traditional dark-field microscopy has already demonstrated the ability to see dense particles under optical resolutions. Dark-field microscopy generally relies on broad-band light sources for illumination of a sample. However, the availability of lasers, which have well-defined properties and are easily manipulated in terms of wavelength, direction, and intensity, has led to the substitution of broadband light sources with lasers in dark-field microscopy. Current developments with laser-scattering microscopes have already demonstrated the ability to see organic particles down to 20 nanometers (nm) and metallic particles down to 5 nm. Additional research has demonstrated that motion of such particles could be resolved to 10 nm or better when using a pin hole filter after the focal spot at the imaging plane.

Scanning confocal microscopes provide three-dimensional images, but only for areas of a sample tainted with fluorescent dye before imaging. However, even the scanning confocal microscope does not reveal optical or other properties of the surfaces which do not have fluorophores. Typical dark-field microscopes are also limited in that they do not provide detailed illumination information; certainly not enough to construct a three-dimensional image.

Scanning Tunneling Microscopy (STM) and Near-Field Scanning Optical Microscopy (NSOM) also only provide information on the surface of a sample, although they have much better resolution than traditional microscopes.

Thus, a need exists in the art for a dark-field laser-scattering microscope which is capable of analyzing single macromolecules in their in-vivo environment and capable of determining exact size, shape, molecular weight, and refractive index.

SUMMARY OF THE INVENTION

The present invention relates to a dark-field laser-scattering microscope for analyzing single macromolecules. More specifically, the present invention relates to a microscope with a variable wavelength, movable, collimated laser for dark-field light scattering of macromolecules in-vivo to reveal characteristics such as size, shape, molecular weight, and refractive index. The microscope is capable of constructing a three-dimensional image of a sample, with the use of a computer, without separating the sample from the in-vivo environment or contaminating the sample with fluorescent dyes.

In one aspect of the present invention, a microscope for analyzing single macromolecules comprises a variable wavelength, movable, collimated laser mounted above a sample and directed at the sample to illuminate the sample; a series of imaging optics to focus scattered light from the sample onto an imaging plane; and a detector to detect the defocusing scattered light of the sample at a second plane.

In another aspect of the invention, the microscope comprises a pin hole screen placed at the imaging plane between the sample and the detector to limit the unwanted scattered light that passes through to the second plane.

In yet another aspect of the invention, the detector is selected from a group consisting of a charge-coupled device (CCD) or Complementary Metal Oxide Semiconductor (CMOS) two-dimensional imaging detector.

In still another aspect of the present invention, a data processing device compiles the data from the detector to determine the characteristics of the sample, including a three-dimensional image, size, molecular weight, and refractive index.

In a further aspect of the present invention, a method for single macromolecule in-vivo microanalysis comprises acts of directing a variable wavelength, movable, collimated laser at a sample from a well-defined angle; focusing the scattered light from the sample through a series of imaging optics and onto an imaging plane; detecting the defocusing scattered light at a second plane with a detector; altering the angle of the laser to collect scattered light from the same area of the sample; and altering the wavelength of the laser to collect scattered light from the same area of the sample.

In a yet further aspect of the invention, the method comprises the act of compiling data from the detector with a data processing device to determine the characteristics of the sample, including a three-dimensional image, size, molecular weight, and refractive index.

In an additional aspect of the present invention, the method comprises the act of placing a pin hole screen between the sample and the detector to limit the scattered light that passes through to the second plane.

In still another aspect of the invention, the method comprises the act of moving the pin hole screen to allow scattered light from different particles to pass through to the second plane.

In another aspect of the present invention, the method comprises the act of moving the sample to cause the laser to illuminate a different area of the sample.

In still another aspect of the present invention, the method comprises the act of moving the laser along with the series of imaging optics to illuminate a different area of the sample.

BRIEF DESCRIPTION OF THE DRAWINGS

The objects, features and advantages of the present invention will be apparent from the following detailed descriptions of the disclosed aspects of the invention in conjunction with reference to the following drawings, where.

Figure 1:
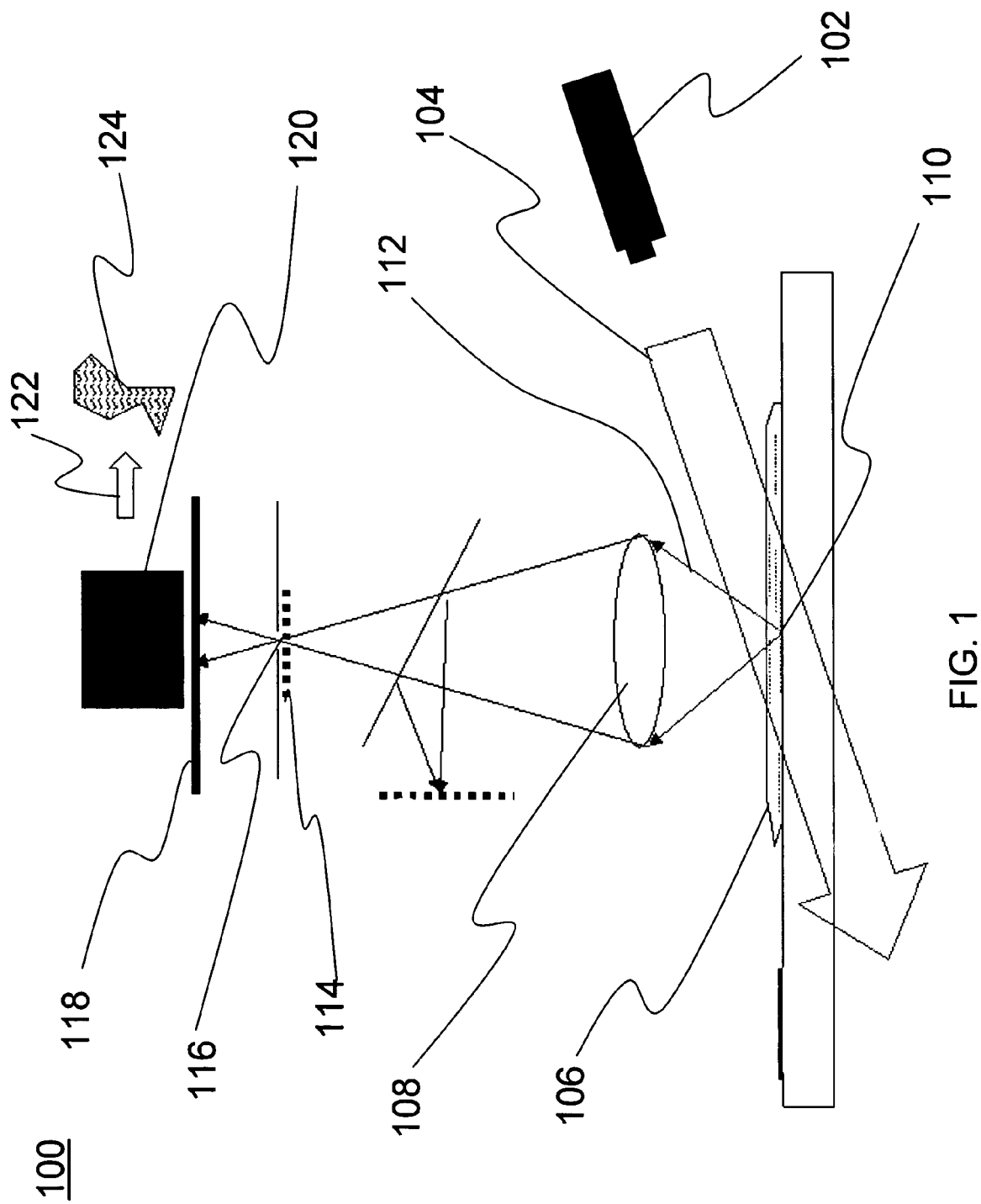
FIG. 1 is a diagram of a microscope in accordance with the present invention, depicting the incoming beam of a variable wavelength laser, which then reflects off of a sample, through a lens, a point pin hole, and to a detector device.

Cross-thatching patterns in the above-referenced drawings are not intended to denote coloration, but rather to distinguish drawing regions.

DETAILED DESCRIPTION

The present invention relates to a dark-field laser-scattering microscope for analyzing single macromolecules. More specifically, the present invention relates to a microscope with a variable wavelength, movable, collimated laser for dark-field light scattering of macromolecules in-vivo to reveal characteristics such as size, shape, molecular weight, and refractive index. The microscope is capable of constructing a three-dimensional image of a sample, with the use of a computer, without separating the sample from the in-vivo environment or contaminating the sample with fluorescent dyes. The following description, taken in conjunction with the referenced drawings, is presented to enable one of ordinary skill in the art to make and use the invention and to incorporate it in the context of particular applications. Various modifications, as well as a variety of uses in different applications, will be readily apparent to those skilled in the art, and the general principles, defined herein, may be applied to a wide range of embodiments. Thus, the present invention is not intended to be limited to the embodiments presented, but is to be accorded the widest scope consistent with the principles and novel features disclosed herein. Furthermore, it should be noted that unless explicitly stated otherwise, the figures included herein are illustrated diagrammatically and without any specific scale, as they are provided as qualitative illustrations of the concept of the present invention.

(1) Introduction

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents that are filed concurrently with this specification and are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

The present invention relates to a dark-field laser-scattering microscope for analyzing single macromolecules. More specifically, the present invention relates to a microscope with a variable wavelength, movable, collimated laser at a defined angle for dark-field light scattering of macromolecules in-vivo to reveal characteristics such as size, shape, molecular weight, and refractive index. The microscope is capable of constructing a three-dimensional image of a sample, with the use of a computer, without separating the sample from the in-vivo environment or contaminating the sample with fluorescent dyes.

(2) Details of Microscope Construction

The microscope provides for analysis of individual single free particles ranging from 10 nanometers (nm) to 500 nm. By varying the angle and wavelength of the laser beam, a computer can reconstruct a three-dimensional picture of the sample, including optical properties such as size, shape, molecular weight, and refractive index. Even more advantageous is the ability of the microscope to characterize single macromolecules in-vivo and in-situ.

In one embodiment of the present invention, as shown in FIG. 1, the microscope 100 is configured such that a laser 102 is directed to shoot a beam 104 through a sample 106 while not directly entering the objective 108 of the microscope 100. The laser beam 104 has a well defined direction, i.e. collimated, to illuminate only particles 110 on the sample 106. Once the beam 104 contacts the sample 106, the beam 104 is scattered 112 in all directions, and collected by the objective optics 108 and focused onto the image plane 114.

To further isolate the scattered light 112 of a specific particle from the scattered light of a different particle, a pin hole device 116 can be used. The pin hole device 116 prevents unfocused light from other particles from entering the second plane 118, thus isolating a desired, focused image of one particle 110 of the sample 106. In one embodiment, the pin hole 116 has a size of several microns. At the second plane 118, a traditional imaging detection device 120 detects the defocused light. The position of the second image plane 115 is chosen for good angular resolution of the scattered light 112, and at the same time gives enough light for the imaging detection device 120 to obtain a sufficient reading.

In one embodiment, the imaging detection device 120 is a highly-sensitive charge-coupled device (CCD). The distribution of the light on the imaging detection device 120 reflects the angular distribution of the scattered light 112 from the specific particle 110. This distribution is determined by the properties of the individual particle 110, such as size or surface refractive index.

In an additional embodiment, the sample 106 can be moved while the pin hole device 116 is fixed. Depending on the practical applications, either the pin hole device 116, the laser 102, or the sample 106 can be moved to obtain scattered light from particles of the sample 106.

In a further embodiment, a beam splitter (not pictured), placed between the laser and the sample, is utilized to provide two channels for imaging and particle analysis. One parallel channel is available to observe the traditional two-dimensional microscope image under either normal illumination or under dark-field laser-scattering illumination. The second channel is for single particle scattering analysis. The pin hole on the top channel could be aimed to a volume of interest and collect the scattering signal only from the tiny volume defined by the pin hole. If used along with other techniques, such as Total Internal Reflection Illumination, volumes as small as 0.05 micrometers cubed ($\mu m^3$) could be detected. Within this small volume and under circumstances where the concentration of macromolecules is not high, it is possible to detect single molecules with dimensions in the 100 nm range.

In one embodiment, the pin hole device 116 can also be moved in the imaging plane 114 to collect different rays of scattered light 112 from the other particles. With an imaging detection device 120 after each pinpoint hole, the data from the imaging detection device 120 can be compiled to determine the size and orientation of each particle 110 as well as the surface quality and shape of a large sample.

In an additional embodiment, once the scattering pattern of the sample is detected by the imaging detection device 120, the laser 102 is moved to illuminate the same area of the sample 106 from a different angle. By providing different scattered light 112 from the same particle 110, the size, shape, molecular weight, and other properties of the sample 106 can be determined.

In a further embodiment, a resolution of the volume detected could be refined with Total Internal Reflection Illumination, and results shows that volume down to 0.7 micrometers ($\mu m$) by 0.7 $\mu m$ by 0.1 $\mu m$ could be detected. Additionally, the possibility of analyzing the size, shape, and molecular weight of molecules in a space of $10^{-19}$ meters cubed ($m^3$) is possible.

In an alternative embodiment, the use of a single quadrant photo diode or linear CCD after the pin hole to detect fast fluctuations of the angular scattering or just one dimensional scattering information. The Mie scattering formula is then used to calculate the size, shape, and molecular weight of the individual particle.

In a still further alternative embodiment, the use of low power objectives is possible, such as a single lens instead of a microscope objective in the microscope tube. This use could provide the orientation information about larger structures on the order of 100s of microns.

In an additional embodiment, once the scattering pattern of the sample 106 is detected by the imaging detection device 120, the wavelength of the laser 102 is changed to illuminate the same area of the sample 106 from the angles that have already been used to collect scattering signals 112 for the wavelength used previously. By providing different laser wavelengths, and collecting the scattered light 112 from the same particles 110, the size, shape, molecular weight, and other properties of the sample 106 can be better determined.

(3) Analysis of the Microscope Data

The data from the imaging detection device 120 is collected by a fast digitizing board (not pictured), processing at 10 mega pixels per second, and the data is then streamed to a computer 122. Finally, the computer 122 compiles the data using typical imaging software and a specific software program designed to analyze the data based on the Mie light scattering theory. From this information, the properties of the sample can be determined, including size, shape, molecular weight, and refractive index.

Once the above acts are finished for the sampling area selected, the data from the imaging detection device 120 can then be collected by a computer 122, which analyzes the data to construct a three-dimensional image 124 of the sample 106, as well as calculate the properties of particular particles inside the sample 106, such as size, molecular weight, and refractive index. The program will analyze the scattering data based on Mie light scattering theory when the wavelength of illumination is changed.

The fluctuations of the scattered light over time indicate the Brownian motion of the tiny particles inside the sample, and if the fluidic property of the sample environment is known, the molecular weight can be calculated.

(4) Specifics of Microscope Components

In one embodiment, an American Optic microscope is used and modified for laser-scattering (American Optics, Inc.; Burlington, Ontario L7R 2J3, Canada). The XY stage is redesigned so that laser beams can be shot at large angles close to 90 degrees to the sample. In one embodiment, objectives with long working distances, such as the Nikon EL WDx40 (Nikon, Inc.; Melville, N.Y. 11747) with an NA of 0.5 and a working distance of 12 millimeters, are used. In this embodiment, lasers have wavelengths at 355 nm, 532 nm, 632 nm, 635 nm, 780 nm and 810 nm. In the present embodiment, the CCD device is an Andor Technology DV877 (Andor Technology, South Windsor, Conn. 06074). The computer utilized in the present embodiment contained a 2.8 Gigahertz processor with 1 Gigabyte of RAM. Additionally, the computer of the present embodiment contained a high-speed disk storage system known as a SATA RAID system.

The software used in the present embodiment to determine the characteristics of the sample has two major parts. The first part is the software known as Andor BASIC, available with the Andor Technology DV877 CCD device, which acquires an image from a CCD device and stores the image in an appropriate format. In the present embodiment, the second part of the software is a program made in-house at Power Energy & Environmental Research Center at the California Institute of Technology, which analyzes the image files based on the Mie scattering theory, and calculates the properties of the sample, including size, weight, and shape.

The samples used in the present embodiment were standard polystyrene beads, purchased from Polysciences (Polysciences, Inc.; Warrington, Pa., 18976), and standard gold particles purchased from Ted Pella (Ted Pella, Inc.; Redding, Calif. 96049). The beads had diameters from 58 nm to 5 microns, and the gold particles have diameter sizes from 20 nm to 200 nm. The samples were diluted from the concentrate to about $10^9$/mL before being analyzed under the microscope setup. Onion cells were also prepared from fresh white onions.

In one embodiment, a low cost security camera was used as the CCD device. In this embodiment, gold particles as low as 25 nm and polystyrene particles down to 58 nm were detected. The probing wavelength was just 532 nm. Even shorter wavelengths of roughly 355 nm could produce single macromolecules as tiny as 40 nm. Additionally, pulsed lasers used along with fast gating cameras could continue to improve the signal to noise ratio and detection of single polymer macromolecules down to 10 nm. In another embodiment, a Complementary Metal Oxide Semiconductor (CMOS) two-dimensional imaging detector is used.

What is claimed is:

1. A microscope for analyzing single macromolecules comprising:
   a variable wavelength, movable, collimated laser mounted above a sample and directed at the sample to illuminate the sample;
   a series of imaging optics to focus scattered light from the sample onto an imaging plane; and
   a detector to detect the defocusing scattered light of the sample at a second plane.

2. The microscope of claim 1, wherein a pin hole screen is placed at the imaging plane between the sample and the detector to limit the unwanted scattered light that passes through to the second plane.

3. The microscope of claim 1, wherein the detector is selected from a group consisting of a charge-coupled device (CCD) or Complementary Metal Oxide Semiconductor (CMOS) two-dimensional imaging detector.

4. The microscope of claim 1, wherein a data processing device compiles the defocused scattered light of the sample at a second plane from the detector to determine the characteristics of the sample, including a three dimensional image, size, molecular weight, and refractive index.

5. A microscope for analyzing single macromolecules comprising:
   a variable wavelength, movable, collimated laser mounted above a sample and directed at the sample to illuminate the sample;
   a series of imaging optics to focus scattered light from the sample onto an imaging plane;
   a detector to detect the defocusing scattered light of the sample at a second plane;
   a pin hole screen placed at the imaging plane between the sample and the detector to limit the unwanted scattered light that passes through to the second plane;
   the detector selected from a group consisting of a charge-coupled device (CCD) or Complementary Metal Oxide Semiconductor (CMOS) two-dimensional imaging detector; and
   a data processing device to compile the data from the detector to determine the characteristics of the sample, including a three-dimensional image, size, molecular weight, and refractive index.

6. A method for single macromolecule in-vivo microanalysis, the method comprising acts of:
   directing a variable wavelength, movable, collimated laser at a sample from a well-defined angle;
   focusing the scattered light from the sample through a series of imaging optics and onto an imaging plane;
   detecting the defocusing scattered light at a second plane with a detector;
   altering the angle of the laser to collect scattered light from the same area of the sample; and
   altering the wavelength of the laser to collect scattered light from the same area of the sample.

7. The method of claim 6, further comprising the act of compiling data from the detector with a data processing device to determine the characteristics of the sample, including a three-dimensional image, size, molecular weight, and refractive index.

8. The method of claim 6, comprising the additional act of placing a pin hole screen between the sample and the detector to limit the scattered light that passes through to the second plane.

9. The method of claim 8, further comprising the act of moving the pin hole screen to allow scattered light from different particles to pass through to the second plane.

10. The method of claim 6, further comprising the act of moving the sample to cause the laser to illuminate a different area of the sample.

11. The method of claim 6, further comprising the act of moving the laser along with the series of imaging optics to illuminate a different area of the sample.

12. The method of claim 6, wherein the detector is selected from a group consisting of a charge-coupled device (CCD) or Complementary Metal Oxide Semiconductor (CMOS) two-dimensional imaging detector.

13. A method for single macromolecule in-vivo microanalysis, the method comprising acts of:
   directing a variable wavelength, movable, collimated laser at a sample from a well-defined angle;
   focusing the scattered light from the sample through a series of imaging optics and onto an imaging plane;
   detecting the defocusing scattered light at a second plane with a detector, the detector being selected from a group consisting of a charge-coupled device (CCD) or Complementary Metal Oxide Semiconductor (CMOS) two-dimensional imaging detector;
   altering the angle of the laser to collect scattered light from the same area of the sample;
   altering the wavelength of the laser to collect scattered light from the same area of the sample;
   compiling data from the detector with a data processing device to determinethe characteristics of the sample, including a three-dimensional image, size, molecular weight, and refractive index;
   placing a pin hole screen between the sample and the detector to limit the scattered light that passes through to the second plane;
   moving the pin hole screen to allow scattered light from different particles topass through to the second plane;
   moving the sample to cause the laser to illuminate a different area of the sample; and
   moving the laser along with the series of imaging optics to illuminate a different area of the sample.

* * * * *